US012731696B2

(12) United States Patent
Okada

(10) Patent No.: US 12,731,696 B2
(45) Date of Patent: Sep. 8, 2026

(54) HEALTH MANAGEMENT DEVICE, HEALTH MANAGEMENT METHOD, AND RECORDING MEDIUM

(71) Applicant: NEC Corporation, Tokyo (JP)

(72) Inventor: Hiroya Okada, Tokyo (JP)

(73) Assignee: NEC CORPORATION, Tokyo (JP)

( * ) Notice: Subject to any disclaimer, the term of this patent is extended or adjusted under 35 U.S.C. 154(b) by 0 days.

(21) Appl. No.: 18/942,946

(22) Filed: Nov. 11, 2024

(65) Prior Publication Data

US 2025/0285771 A1 Sep. 11, 2025

(30) Foreign Application Priority Data

Mar. 7, 2024 (JP) ................................ 2024-035053

(51) Int. Cl.
*G16H 50/80* (2018.01)
*G16H 10/60* (2018.01)
*G16H 50/20* (2018.01)

(52) U.S. Cl.
CPC ............ *G16H 50/80* (2018.01); *G16H 10/60* (2018.01); *G16H 50/20* (2018.01)

(58) Field of Classification Search
None
See application file for complete search history.

(56) References Cited

U.S. PATENT DOCUMENTS 11,322,260 B1 * 5/2022 Jain ...................... H04W 4/021
2016/0308969 A1 * 10/2016 Aihara ................. G06F 16/951
2020/0357503 A1 * 11/2020 Sugaya ............... A61B 5/1128

(Continued)

FOREIGN PATENT DOCUMENTS

CN 117792478 A * 1/2024 ............ H04B 7/185
JP 2022-032426 A 2/2022
KR 10-2356778 B1 * 4/2021 ............ G06F 21/32

OTHER PUBLICATIONS

Garshnek et al. Telemedicine Applied to Disaster Medicine and Humanitarian Response: History and Future; Proceedings of the 32nd Hawaii International Conference on System Sciences—1999.*

(Continued)

*Primary Examiner* — David J Stoltenberg
(74) *Attorney, Agent, or Firm* — Sughrue Mion, PLLC

(57) ABSTRACT

A health management device includes an environment storage unit storing environmental information in which a state of a region is associated with a disease in the state, and acquires user identification information, acquires biometric information of the user, authenticates the user by comparing biometric information associated with the user identification information with the acquired biometric information, and acquires movement history information concerning each area through which the user passed. The health management device acquires the environmental information concerning area through which the user passed from the environment storage unit, based on the movement history information, calculates a probability that the user is infected with the disease based on the biometric information and environmental information, and outputs persuasion information for persuading the user to seek a medical consultation if the probability is equal to or greater than a threshold value, whereby assisting the user in decision-making to see a doctor.

14 Claims, 6 Drawing Sheets

(56) References Cited

U.S. PATENT DOCUMENTS

| | | | | |
|---|---|---|---|---|
| 2021/0319894 | A1* | 10/2021 | Sobol | G16H 50/30 |
| 2021/0319914 | A1* | 10/2021 | Roh | G16H 40/67 |
| 2022/0240779 | A1* | 8/2022 | Peyman | A61B 5/441 |
| 2022/0392629 | A1* | 12/2022 | Reddy | G06V 40/172 |
| 2023/0087729 | A1* | 3/2023 | Goldstein | G16H 50/70 455/456.1 |
| 2023/0120218 | A1 | 4/2023 | Maruyama et al. | |
| 2023/0335287 | A1* | 10/2023 | Miller | G16H 40/67 |
| 2023/0411008 | A1* | 12/2023 | Khanzada | G16H 10/65 |
| 2024/0233367 | A1* | 7/2024 | Motayed | G01S 13/90 |

OTHER PUBLICATIONS

Howsalya Devi, et al. 5G Technology in Healthcare and Wearable Devices: A Review, Sensors 2023, 23, 2519. https://doi.org/10.3390/s23052519.*

* cited by examiner

100
USER DB
31
1
5
INPUT TERMINAL
SERVER
2
5
3
SATELLITE SYSTEM
ENVIRONMENT DB
REPORT DB
32
33
4
HOSPITAL SYSTEM

FIG. 3

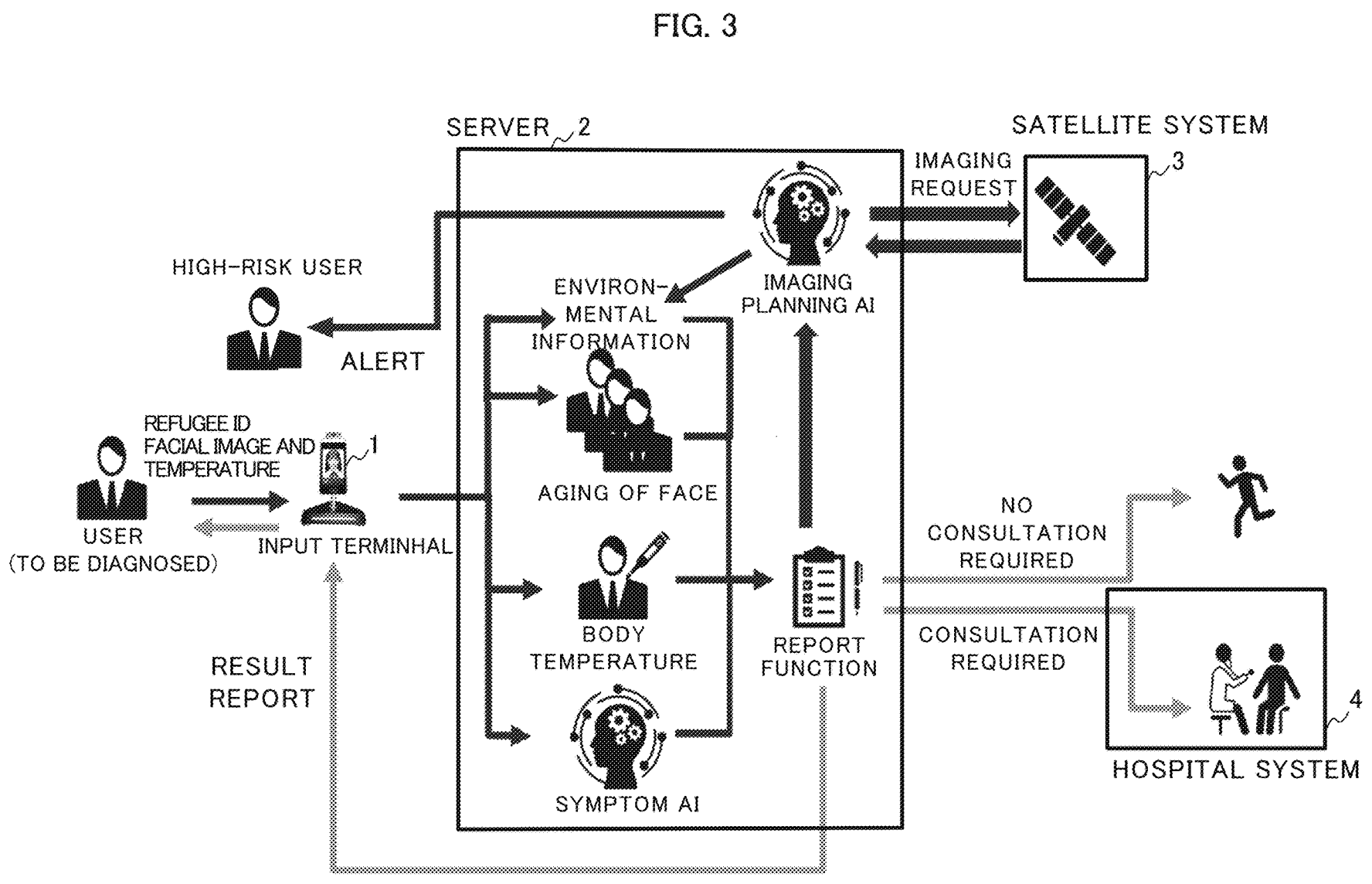

SATELLITE SYSTEM
3
IMAGING REQUEST
SERVER 2
IMAGING PLANNING AI
ENVIRON-MENTAL INFORMATION
AGING OF FACE
BODY TEMPERATURE
SYMPTOM AI
REPORT FUNCTION
NO CONSULTATION REQUIRED
CONSULTATION REQUIRED
HOSPITAL SYSTEM
4
HIGH-RISK USER
ALERT
1
INPUT TERMINHAL
REFUGEE ID
FACIAL IMAGE AND TEMPERATURE
USER (TO BE DIAGNOSED)
RESULT REPORT

HEALTH MANAGEMENT DEVICE, HEALTH MANAGEMENT METHOD, AND RECORDING MEDIUM

TECHNICAL FIELD

This disclosure relates to a technique for performing a health management for a user.

BACKGROUND ART

Currently, artificial satellites are used for various purposes, and are used in some cases to assess disaster and other situations and a warfare condition.

Moreover, conventionally, systems are known to consider an epidemic state of an infectious disease in each region in a case of providing healthcare services. Patent document 1 describes a system for obtaining movement history information for each individual and determining an infection status of each individual with the infectious disease based on this movement history information.

Patent Document 1: Japanese Patent Application Laid-Open under No. 2022-032426

SUMMARY

Currently, although the refugee ID system has enabled material support services to operate efficiently, medical services are still inefficient due to a shortage of doctors, indicating that there is significant room for improvement.

One object of the present disclosure is to assist users with appropriate health management using information of areas.

In order to solve the problems described above, according to an example aspect of the present invention, there is provided a health management device including:

- at least one memory configured to store instructions;
- an environment storage unit configured to store environmental information in which a state of a region is associated with a disease in the state; and
- at least one processor configured to execute the instructions to:
- acquire user identification information for identifying a user;
- acquire biometric information of the user;
- authenticate the user by comparing biometric information associated with the user identification information in advance with the biometric information which is acquired;
- acquire movement history information concerning each area through which the user passed, based on the user identification information;
- acquire the environmental information of each area through which the user passed from the environment storage unit, based on the movement history information;
- calculate a probability that the user is infected with the disease based on the biometric information and the environmental information; and
- output persuasion information for persuading the user to seek a medical consultation of a doctor in a response to the probability that is equal to or greater than a threshold value.

According to another example aspect of the present invention, there is provided a health management method to be executed by a health management device including an environment storage unit configured to store environmental information in which a state of a region is associated with a disease in the state, the health management method including:

- acquiring user identification information for identifying a user; performing a biometric information acquisition process for acquiring biometric information of the user;
- authenticating the user by comparing biometric information associated with the user identification information in advance with the biometric information acquired by the biometric information acquisition process;
- acquiring movement history information concerning each area through which the user passed, based on the user identification information;
- acquiring the environmental information of each area through which the user passed from the environment storage unit, based on the movement history information;
- calculating a probability that the user is infected with the disease based on the biometric information and the environmental information; and
- outputting persuasion information for persuading the user to seek a medical consultation of a doctor in a response to the probability that is equal to or greater than a threshold value.

According to still another example aspect of the present invention, there is provided a non-transitory computer-readable program causing a computer to perform a process, wherein a health management device includes an environment storage unit configured to store environmental information in which a state of a region is associated with a disease in the state, and the computer, the process including:

- acquiring user identification information for identifying a user;
- performing a biometric information acquisition process for acquiring biometric information of the user;
- authenticating the user by comparing biometric information associated with the user identification information in advance with the biometric information acquired by the biometric information acquisition process;
- acquiring movement history information concerning each area through which the user passed, based on the user identification information;
- acquiring the environmental information of each area through which the user passed from the environment storage unit, based on the movement history information;
- calculating a probability that the user is infected with the disease based on the biometric information and the environmental information; and
- outputting persuasion information for persuading the user to seek a medical consultation of a doctor in a response to the probability that is equal to or greater than a threshold value.

EFFECT

According to the present disclosure, it is possible to assist users with appropriate health management using information of areas.

BRIEF DESCRIPTION OF THE DRAWINGS

FIG. 3 is a diagram schematically illustrating a process by the server.

EXAMPLE EMBODIMENTS

Preferred example embodiments of the present disclosure will be described with reference to the accompanying drawings.

Example Embodiments

Configuration

Figure 1:
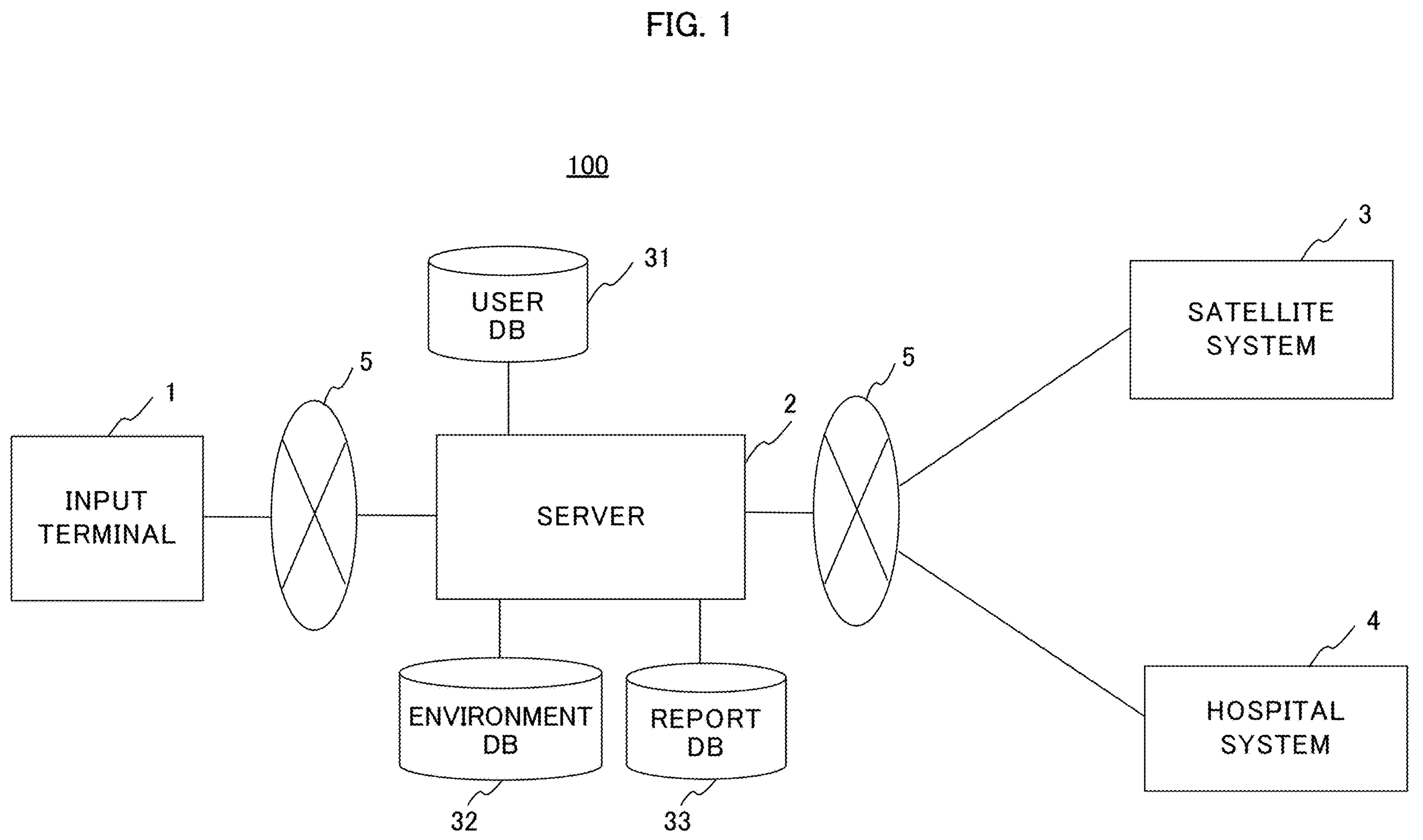
FIG. 1 illustrates an example of a schematic configuration of a health management system.

FIG. 1 is an example of a schematic configuration of a health management system 100 to which a server of the present disclosure is applied. The health management system 100 is a system which assists users in managing their health, and provides efficient medical care, by automating counseling to be an initial medical examination by using IDs which identify respective users, and by prioritizing examinations and treatments of patients who have been detected to have a disease.

Incidentally, the health management system 100 can also be applied as an environmental information collection system which appropriately collects environmental information concerning a state of each region by making highly accurate imaging requests to satellites.

The user in this disclosure is, for instance, a refugee temporarily staying in a refugee camp or the like. Moreover, the health management system 100 utilizes refugee IDs and cards on which refugee ID are recorded in a refugee ID system operated by the United Nations Organization and.

In the health management system 100, an input terminal 1, a server 2, a satellite system 3, and a hospital system 4 are communicably connected via a network 5 such as the Internet. The input terminal 1 is an information processing device installed in a refugee camp or the like in each region, and can acquire the refugee ID from the card which a user holds over the input terminal 1. In addition, the input terminal 1 is provided with a camera and a thermographic camera, and can acquire a face image and a body temperature of the user.

The server 2 is an information processing device which processes, stores, and exchanges various types of data, analyzes information acquired from the input terminal 1 and the environmental information to be described later to diagnose whether the user is suffering from a predetermined disease, and outputs information for persuading the user to seek a medical consultation of a doctor if necessary. Here, the user who suffers from a predetermined disease is also referred to as an infected user. In addition, the server 2 sends a request to the satellite system 3 for imaging of each area through which the infected user has passed.

The satellite system 3 is formed by an information processing device which processes, stores, and exchanges various types of data. The satellite system 3 is a system for managing an operation of an artificial satellite, and records changes by imaging the same point at a specified interval using the artificial satellite and captures images at a predetermined point using the artificial satellite in response to an emergency imaging request. Specifically, if that imaging request is received from the server 2, the satellite system 3 captures images of an area specified by the artificial satellite, and transmits the captured images or videos as satellite images to the server 2.

The hospital system 4 is formed by an information processing device for processing, storing and exchanging various types of data. The hospital system 4 is a system which manages medical appointments and the like of hospitals. Specifically, in a case where the hospital system 4 acquires information such as the refugee ID of each infected user, a symptom, and a disease name from the server 2, the hospital system 4 makes each medical appointment, and sends each date and time of the medical appointment to the server 2.

Figure 2:
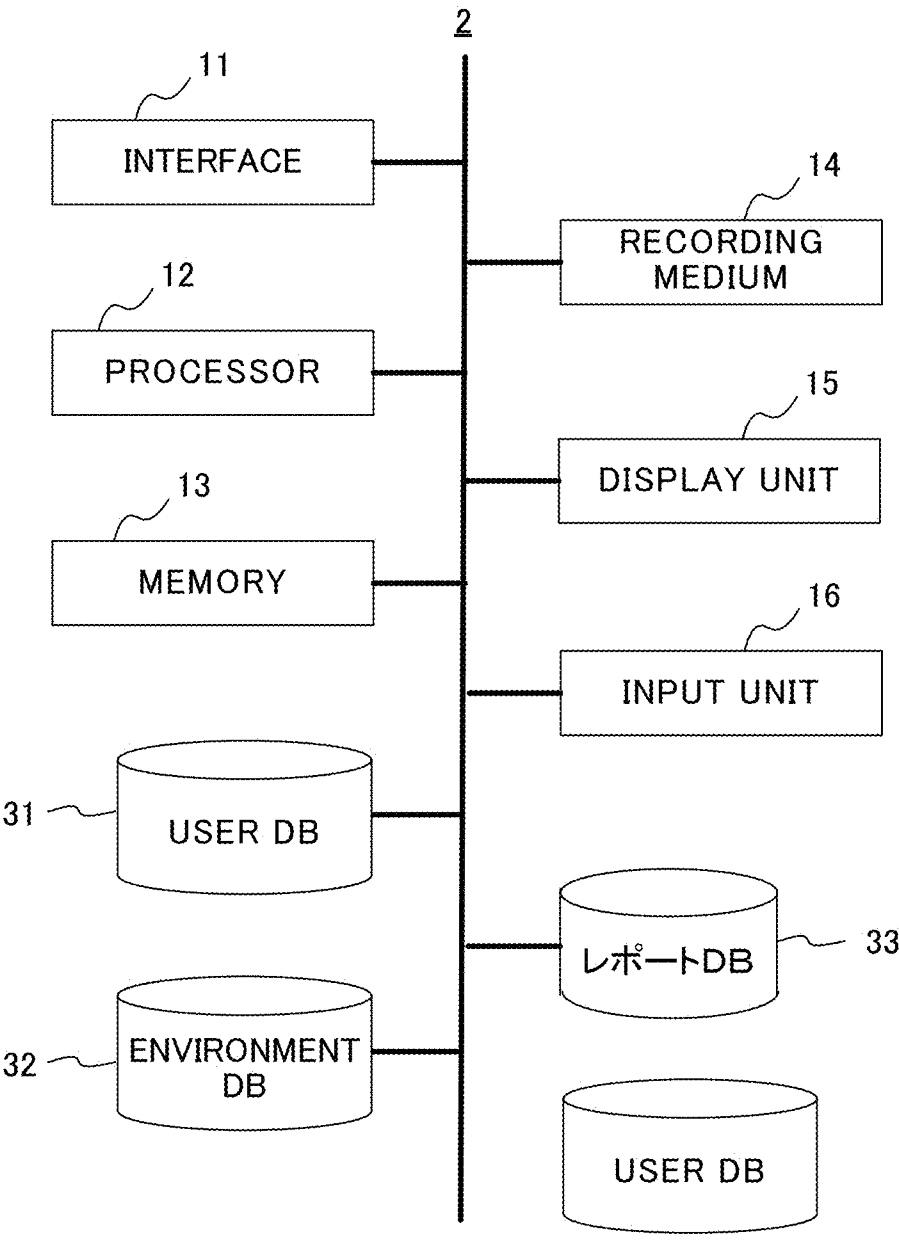
FIG. 2 illustrates an example of a hardware configuration of a server.

FIG. 2 is a block diagram illustrating an example of a hardware configuration of the server 2. As illustrated in FIG. 2, the server 2 includes an interface (Interface) 11, a processor 12, a memory 13, a recording medium 14, a display unit 15, and an input unit 16. Note that these elements, a user DB 31, an environment DB 32, and a report DB 33 are mutually connected via a bus.

The interface 11 exchanges data with the input terminal 1, the satellite system 3, and the hospital system 4. Moreover, the interface 11 is used by the server 2 to exchange data with a predetermined device connected by wired or wireless communication.

The processor 12 is a computer such as a CPU (Central Processing Unit) and controls the entire server 2 by executing programs prepared in advance. Incidentally, as the processor 12, the CPU, a GPU (Graphics Processing Unit), a DSP (Digital Signal Processor), a MPU (Micro Processing Unit), a FPU (Floating Point number Processing Unit), a PPU (Physics Processing Unit), a TPU (Tensor Processing Unit), a quantum processor, a microcontroller, or a combination thereof can be used.

The memory 13 is formed by a ROM (Read Only Memory) and a RAM (Random Access Memory). The memory 13 stores programs executed by the processor 12. Moreover, the memory 13 is used as a working memory during executions of various processes performed by the processor 12.

The recording medium 14 is a non-volatile and non-transitory recording medium such as a disk-shaped recording medium or a semiconductor memory, and is formed to be detachable from the server 2. The recording medium 14 records various programs executed by the processor 12. In a case where the server 2 executes a health management process or an environmental information collection process, corresponding programs recorded in the recording medium 14 are loaded into the memory 13 and executed by the processor 12.

The display unit 15 is an LCD (Liquid Crystal Display), for instance, and displays each predetermined image. The input unit 16 is a keyboard, a mouse, a touch panel, or the like, and is used by an operator who manages the server 2.

The user DB 31 stores user information in which the refugee ID is associated with a name, biometric information, contact details, movement history information, a diagnosis date and time and, a diagnosis result, and an appointment status. The biometric information is information necessary for facial recognition, for instance, a face image of each user registered in advance. The contact details may be a telephone number, an e-mail address, or the like to provide various notifications to the user. The movement history information is information concerning areas through which the user has passed during the movement, as well as dates and times of a visit of the user to each area. The diagnosis date and time is a date and time in a case where the user is diagnosed whether or not the user is suffering from the disease by analyzing the biometric information obtained from the input terminal 1 and the environmental information described below. The diagnosis result is a result from diagnosing whether or not the user is suffering from the disease. The appointment status is a status of the medical appointment made to the hospital system 4 in a case where the user is infected with the disease, and is information of the hospital name and the date and time of the medical appointment.

The environment DB 32 stores environmental information concerning the state of each region. Specifically, the environmental information is information concerning the state of each region and the disease related to that state. The state of each region may indicate, for instance, a natural disaster such as a flood, a fire, or a drought, a human-made disaster such as bombing, a landmine, and an epidemic of an infectious disease, a secondary disaster such as a fire and a power outage which are associated with the disaster, or the like. An example of the environmental information is information in which the flood as the state of a region A is associated with a pathogen which is causing an increase in the number of infected in the region A due to the flood. Another example of the environmental information is information in which a fire as the state of a region B is associated with a large number of injuries in the region B due to the fire. Another example of the environmental information is information in which a landmine as a state in a region C is associated with a large number of leg injuries caused by metal fragments in the region C due to the landmine. Another example of environmental information is information in which the epidemic of the infectious disease as a state in a region D is associated with the name of the infectious disease which is prevalent in the region D. Note that the environmental information may be associated with a plurality of states in one area, or may be associated with a plurality of diseases for each state.

The report DB 33 stores report information in which the refugee ID of the infected user is associated with the symptom and disease name, the movement history information, the state of each area through which the infected user passed, and an outbreak region. The outbreak region is an area where the infected user encountered a state leading to the disease among areas through which the infected user passed. Note that in a case where the outbreak region cannot be specified, it may not be included in the report information. Moreover, the report information may not include movement history information and the state of each area through which the infected user passed, as long as the report information includes the outbreak region and the state of the outbreak region.

Note that the server 2 of the present disclosure includes user DB 31, environment DB 32, and report DB 33 for convenience of explanation, but are not limited to these databases. A type of a DB and a data structure of the DB are arbitrary as long as necessary data can be obtained. For instance, the user DB 31 may be formed by three DBs: the user DB for storing each refugee ID, the name, the biometric information, and the contact details; a movement history DB for storing the refugee ID and the movement history information; and an appointment DB for storing the diagnosis date and time, the diagnosis result, and the status of the medical appointment.

FIG. 3 is a diagram schematically illustrating a health management process and an environmental information collection process which are performed by the server 2. As illustrated in FIG. 3, the user who is a subject of an initial counseling diagnosis needs to go to the refugee camp, the hospital, or a government facility where the input terminal 1 is installed, in a case where the user is feeling unwell. Upon arrival, the user holds a card of the user over the input terminal 1 and a face image of the user is captured. Accordingly, the input terminal 1 acquires the refugee ID, the face image, and the body temperature of the user, and transmits the acquired information to the server 2. The server 2 authenticates the user based on the information acquired from the input terminal 1, and performs the initial consultation diagnosis in a case where there is no problem.

In the initial counseling diagnosis, a probability that the user has suffered from a predetermined disease is calculated, and it is determined that the user is infected with the predetermined disease in a case where the probability is equal to or greater than a threshold value. On the other hand, in a case where the probability is less than the threshold value, it is determined that the user is not suffering from the predetermined disease. Specifically, the initial counseling diagnosis will be described in detail later. In the initial counseling diagnosis, the symptom is specified and the disease name is estimated, based on based on respective determination results of aging of face, the body temperature, and an initial symptom by a symptom AI, and the environmental information of each area through which the user has passed, and the probability that the user is suffering from the predetermined disease is calculated. Note that in a case where there is no environmental information of each area through which the user has passed, the server 2 specifies the symptom and estimate the disease name based on respective determination results of the aging of face, the body temperature, and the initial symptom by the symptom AI, and then calculates the probability of suffering from the predetermined disease. Here, the AI (Artificial Intelligence) is a technique which makes a computer perform intelligent actions such as an inference, a decision-making, and the like which are carried out by humans using intelligence. As will be described later, the symptom Al is a technique that uses machine-learning to determine whether or not initial symptoms of the disease have appeared.

In a case where the initial-counseling diagnoses that the user has suffered from the predetermined disease, the server 2 updates the report DB 33 by storing information in which the refugee ID of the infected user is associated with the symptom and the disease name, the movement history information, the state of the passing area, and the outbreak region. In addition, in a case where the user is diagnosed as suffering from the predetermined disease by the initial counseling diagnosis, the server 2 makes a medical appointment for the infected user by transmitting information including the refugee ID, the name, and the symptom, the disease name, and the like of the infected user to the hospital system 4. Next, the server 2 updates the user DB 31 by storing the diagnosis result, the diagnosis date and time, and the status of the medical appointment in the user DB 31 by associating with the refugee ID of the infected user, and reports necessity of counseling by the doctor, the date and time for the medical appointment made to the hospital as a result of the initial counseling diagnosis to the infected user by referring to the contact details. The infected user who has confirmed the report visits the hospital on the date and time of the medical appointment to be examined by the doctor.

On the other hand, in a case where the initial counseling diagnosis determines that the user is not suffering from the predetermined disease, the server 2 updates the user information by storing the diagnosis result and the diagnosis date and time in the user DB 31 in association with the refugee ID of the user, and reports that the medical examination by the doctor is unnecessary as a result of the initial counseling diagnosis, to the user by referring to the contact details. In this case, the user does not go to the hospital to be examined by the doctor. Accordingly, by having server 2 perform the initial counseling diagnosis, it is possible to give the infected user a higher priority for the medical consultation by the doctor, thereby improving efficiency of medical care and also preventing a delay of the medical consultation due to a shortage of doctors.

A report function of the server 2 refers to the report DB 33, and provides the movement history information of the infected user, the outbreak region, and the like to an imaging plan Al in a case where the infected user has passed through an area to be surveyed by the artificial satellite. The imaging plan AI examines a recommended imaging area based on the provided information, creates an imaging request specifying an area which is preferable to be captured for checking the state of that area, and transmits the created imaging request to the satellite system 3. If the imaging request is acquired from the server 2, the satellite system 3 captures the area designated by the artificial satellite, and transmits the satellite images to the server 2. The server 2 acquires the environmental information by analyzing the acquired satellite images, and updates the environment DB 32 by the acquired environmental information. The environmental information stored in the environment DB 32 are utilized for the initial counseling diagnosis of other users.

Moreover, the imaging plan Al refers to the user DB 31 based on the movement history information of the infected user and the outbreak region, specifies, as the high-risk user, the user who visited the same area at the same timing as the infected user, and alerts the high-risk user that the high-risk user may have suffered from the same disease as the infected user.

As described above, the health management system 100 performs the initial counseling diagnosis of the user in consideration of the environmental information, and also acquires new environmental information in response to the imaging request which is based on the result of the initial counseling diagnosis. That is, there is a mechanism in which the environmental information is circulated among the functions of the health management system 100.

Figure 4:
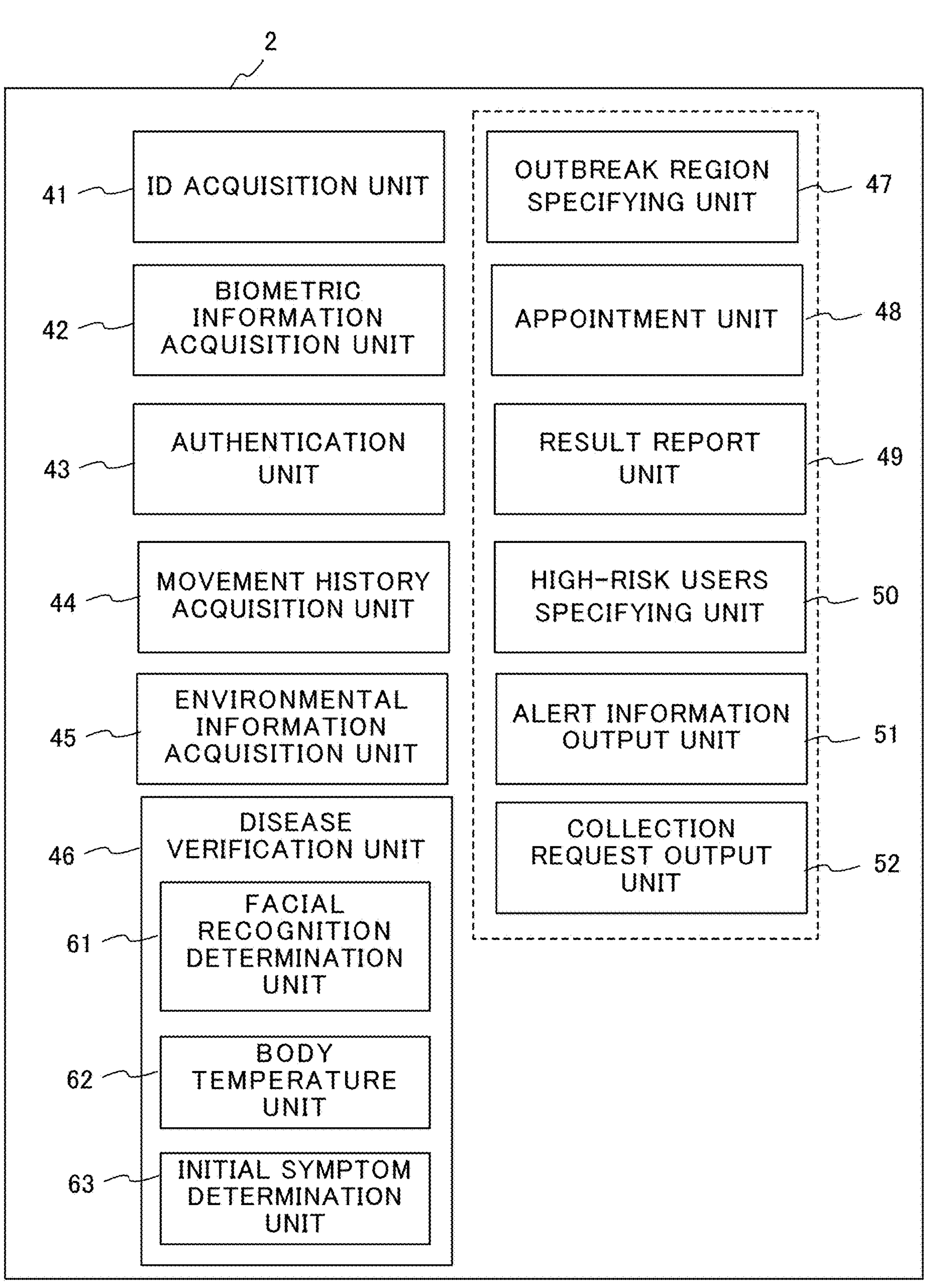
FIG. 4 is a block diagram illustrating an example of a functional configuration of the server.

FIG. 4 is a block diagram illustrating an example of a functional configuration of the server 2. The server 2 functionally includes an ID acquisition unit 41, a biometric information acquisition unit 42, an authentication unit 43, a movement history acquisition unit 44, an environmental information acquisition unit 45, a disease verification unit 46, an outbreak region specifying unit 47, an appointment unit 48, a result report unit 49, a high-risk user specifying unit 50, an alert information output unit 51, and a collection request output unit 52. The ID acquisition unit 41, the biometric information acquisition unit 42, the authentication unit 43, the movement history acquisition unit 44, the environmental information acquisition unit 45, the disease verification unit 46, the outbreak region specifying unit 47, the appointment unit 48, the result report unit 49, the high-risk user specifying unit 50, the alert information output unit 51, and the collection request output unit 52 are realized by the processor 12 executing corresponding programs.

Note that the report function and a function of the imaging plan Al depicted in FIG. 3 correspond to the outbreak region specifying unit 47, the appointment unit 48, the result report unit 49, the high-risk user specifying unit 50, the alert information output unit 51, and the collection request output unit 52 depicted in FIG. 4.

The ID acquisition unit 41 acquires the refugee ID of the user to be the subject from the input terminal 1. The biometric information acquisition unit 42 acquires the face image and the body temperature of the user to be the subject from the input terminal 1.

The authentication unit 43 performs the authentication by comparing the face image which is associated with the refugee ID in advance acquired from the input terminal 1, with the face image acquired from the input terminal 1. The face image associated with the refugee ID in advance is acquired from the user DB 31 based on, for instance, the refugee ID. Specifically, the authentication unit 43 authenticates the user to be the subject by acquiring features related to facial components such as eyes, a nose, and a mouth from the face image and matching the face images.

The movement history acquisition unit 44 acquires the movement history information from the user DB 31 based on the refugee ID of the user to be the subject. The movement history information is information concerning each area through which the user passed during the movement and a date and time in a case where the user visited the area. Note that the information indicating the area can be arbitrarily set such as a latitude and longitude, an address, or the like.

The environmental information acquisition unit 45 acquires the environmental information of the area through which the user has moved from the environment DB 32 based on the movement history information of the user to be the subject. The environmental information is information which matches the state of the region and the disease in the state. Specifically, the environmental information is information in which information specifying the area such as the latitude and longitude, information indicating the state of the region such as the flood, and information concerning the disease such as the name of the disease of numerous outbreaks.

The disease verification unit 46 performs verification to detect a disease, such as specifying symptoms, calculating a probability of suffering from the disease, and estimating the name of the disease, and the like for the user to be the subject based on the biometric information obtained from the input terminal 1. In a case where the environmental information acquisition unit 45 acquires the environmental information, the disease verification unit 46 performs the verification based on the biometric information and the environmental information.

The disease verification unit 46 includes a facial recognition unit 61, a body temperature determination unit 62, and an initial symptom determination unit 63. The face determination unit 61 compares the face image acquired from the input terminal 1 with an aging face image based on a face matching by another service, and determines whether there are any sudden changes in a shape or color of a facial area.

The body temperature determination unit 62 determines whether or not the body temperature acquired from the input terminal 1 is abnormal, for instance, whether the body temperature is equal to or more than a threshold value. The initial symptom determination unit 63 is a function by the symptom AI depicted in FIG. 3, and determines in response to the input of the face image whether or not the initial symptom of the disease has appeared, based on the face image of the user to be the subject by using the machine learning model which has been trained to output whether or not the initial symptom of the disease has appeared on the face.

The disease verification unit 46 determines that the user to be the subject is unlikely to be suffering from the predetermined disease in a case of no abnormalities in all three viewpoints based on respective results of the face determination unit 61, the body temperature determination unit 62, and the initial symptom determination unit 63. At this time, the disease verification unit 46 may calculate the probability of suffering from the disease in a numerical value acquired by a predetermined calculation formula. Note that in a case where the environmental information acquisition unit 45 has acquired the environmental information, the disease verification unit 46 determines the probability that the user to be the subject is infected with the disease, in consideration of the state of the area through which the user to be the subject has passed and the disease in that state. If it is determined that the user is unlikely to have the disease or if the calculated probability is less than a threshold value, the disease verification unit 46 diagnoses that the user to be the subject is not suffering from the predetermined disease, that is, the user is healthy. In a case of diagnosing that the user does not suffer from the predetermined disease, the disease verification unit 46 updates the user DB 31 by storing the refugee ID and the name of the user, a diagnosis result, and a diagnosis date and time.

On the other hand, in a case of detecting an abnormality in one or more viewpoints based on respective results of the facial recognition unit 61, the body temperature determination unit 62, and the initial symptom determination unit 63, the disease verification unit 46 determines that the probability of the user to be the subject being infected with the predetermined disease is high. Note that in a case where the environmental information acquisition unit 45 has acquired the environmental information, the disease verification unit 46 estimates the disease name in consideration of the state of the area through which the user to be the subject has passed, and the disease in the state. For instance, in a case where it is recognized from the environmental information that Influenza A is prevalent in the region D and the user to be the subject exhibits a symptom of fever, the disease verification unit 46 estimates the disease to be Influenza A. The disease verification unit 46 diagnoses that the user to be the subject has infected with the predetermined disease in a case of determining that the probability that the user is infected with the disease or in a case of determining that the calculated probability is equal to or greater than the threshold value. In other words, the disease verification unit 46 diagnoses that the disease of the user to be the subject is detected.

In a case of diagnosing that the user to be the subject is infected with the predetermined disease, the disease verification unit 46 updates the report DB 33 by storing information that the refugee ID of the infected user is associated with the symptom and the disease name, the movement history information, the state of the area through which the infected user passed, and the outbreak region.

The outbreak region specifying unit 47 refers to the report DB 33, and specifies the are where the infected user encountered a state leading to the disease as the outbreak region. For instance, in a case where the presumed disease name is an enterohemorrhagic escherichia coli infection and the infected user is passing through the region A where the escherichia coli is increasing due to the flood from the report DB 33, the outbreak region specifying section 47 specifies the region A as the outbreak region. In a case of specifying the outbreak region, the outbreak region specifying unit 47 updates the report DB 33 by further storing information of the outbreak region and the date and time if the infected user visited the outbreak region in the report information corresponding to the infected user.

In response to the diagnosis by the disease verification unit 46 that the user to be the subject is infected with the predetermined disease, the appointment unit 48 makes a medical appointment for the infected user by transmitting information including the refuge ID and the name of the infected user, the symptom, the disease name, and the like to the hospital system 4. If the medical appointment is completed, the appointment unit 48 updates the user DB 31 by storing the diagnosis result, the diagnosis date and time, and the status of the medical appointment in association with the refugee ID of the infected user.

The result report unit 49 reports that the medical examination is not necessary to the user by referring to the contact details if the disease verification unit 46 diagnoses the user to be the subject as healthy. On the other hand, if the user to be the subject is diagnosed by the disease verification unit 46 as suffering from the predetermined disease, the result notification unit 49 reports that the medical examination by the doctor is necessary and that the date and time of the medical appointment have been scheduled, the user by referring to the contact details. As described above, by reporting the result, it is possible to assist the infected user in making a decision to see the doctor.

The high-risk user specifying unit 50 refers to the user DB 31 based on the movement history information and the outbreak region of the infected user stored in the report DB 33, and specifies each user who visited the same area at the same timing as the infected user, to be the high-risk user. The same timing as the infected user is within a predetermined time in reference to a visited date and time of the infected user, and the time is arbitrarily set according to the disease suffered such as one day, one week, one month, or the like.

The alert information output unit 51 transmits alert information indicating that the disease may be the same as that of the infected user to the contact details of the high-risk user. Thus, even in a case where the symptom has not yet appeared or the symptom is mild, the high-risk user goes to the hospital, explains a situation, and receives a medical examination. Therefore, it is possible for the high-risk user to be treated at an early stage before the symptom of the high-risk user worsen.

The collection request output unit 52 refers to the report DB 33, and if the infected user is passing through the area to be surveyed by the artificial satellite, the collection request output unit 52 examines a recommended imaging area based on the movement history information of the infected user and the outbreak region, creates an imaging request which specifies the area to be captured for checking the state, and transmits the created imaging request to the satellite system 3. If the imaging request is acquired from the server 2, the satellite system 3 captures the area designated by the artificial satellite, and transmits the satellite images to the server 2. The server 2 acquires the environmental information by analyzing the acquired satellite images, and updates the environment DB 32. Note that the satellite system 3 may report the designated area included in the imaging request and the state of the designated area to government agencies such as ministries and local authorities for use in a disaster management.

In the configuration described above, the ID acquisition unit 41, the biometric information acquisition unit 42, the authentication unit 43, the movement history acquisition unit 44, the environmental information acquisition unit 45, the disease verification unit 46, the outbreak region specifying unit 47, the appointment unit 48, the result report unit 49, the high-risk user specifying unit 50, the alert information output unit 51, the facial recognition unit 61, the body temperature determination unit 62, and the initial symptom determination unit 63 correspond to respective examples of a user identification information acquisition means, a biometric information acquisition means, an authentication means, a movement history acquisition means, an environmental information acquisition means, a disease verification means, an outbreak region specifying means, an appointment means, a persuasion information output means, a high-risk user specifying means, an alert information output means, a facial recognition means, a body temperature determination means, and an initial symptom determination means in this disclosure.

Moreover, the environment DB 32 and the report DB 33 included in the server 2 correspond to respective examples of an environment storage unit and a report storage unit.

Health Management Process

Figure 5:
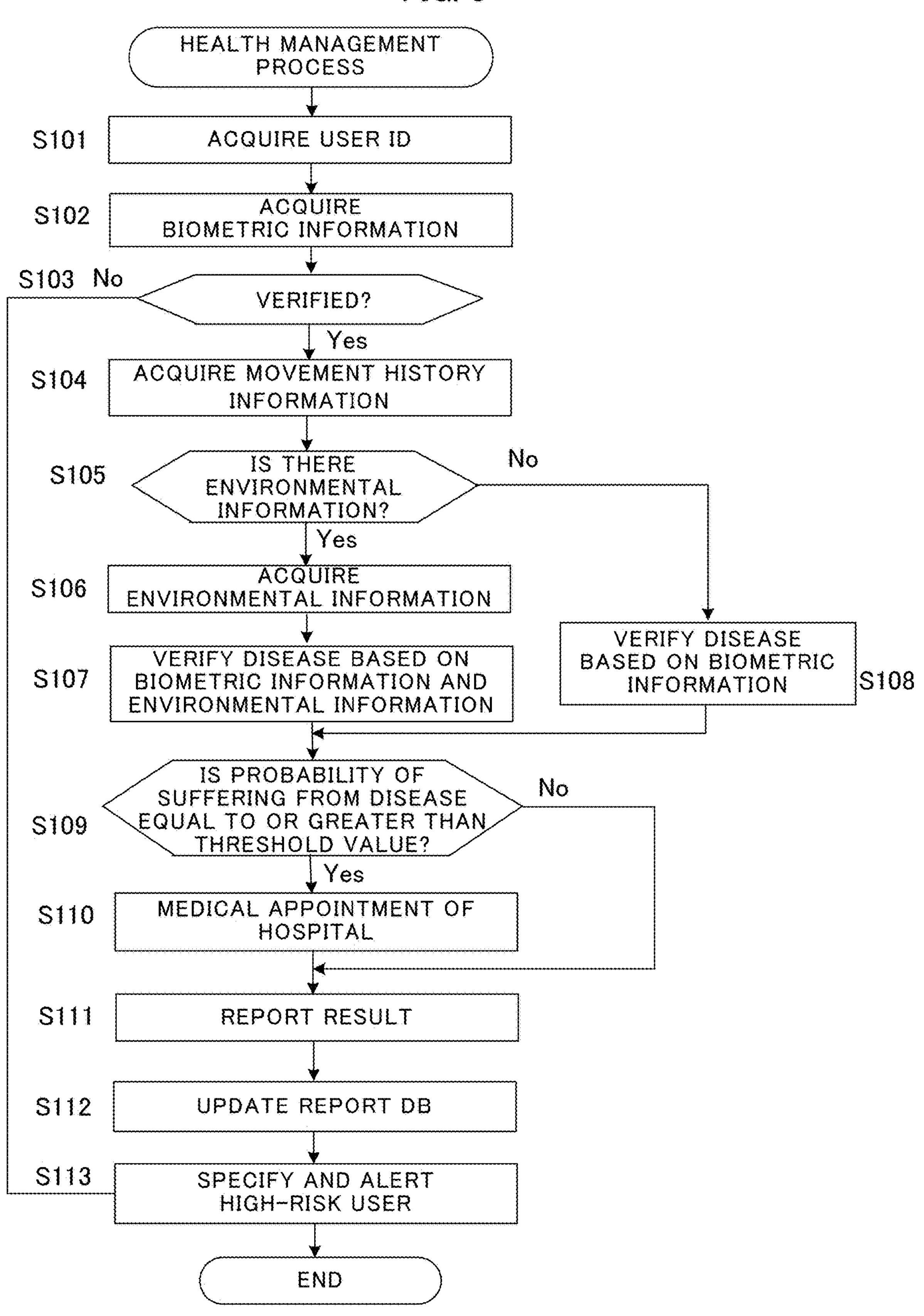
FIG. 5 illustrates a flowchart of a health management process.

Next, a health management process by the server 2 will be described. FIG. 5 is a flowchart of the health management process performed by the server 2. This health management process is realized by the processor 12 illustrated in FIG. 2 executing a corresponding program prepared in advance.

If the user who is the subject of the medical consultation is unwell, the user goes to a predetermined administrative facility where the input terminal 1 is installed. If the user arrives at the predetermined administrative facility, the user holds the card of the user over the input terminal 1, and the face image of the user is captured. Accordingly, the input terminal 1 acquires the refugee ID of the user, the face image, and the body temperature, and transmits the acquired information to the server 2.

The server 2 first acquires the refugee ID from the input terminal 1 (step S101). Moreover, the server 2 acquires the face image and the body temperature as the biometric information from the input terminal 1 (step S102). The server 2 authenticates the user by comparing the face image associated with the refugee ID in advance with the face image acquired from the input terminal 1. If the user is not a person in question (step S103; No) as a result of the authentication, the server 2 terminates the health management process. On the other hand, if the user is the person in question (step S103; Yes) as the result of the authentication, the server 2 acquires the movement history information from the user DB 31 based on the refugee ID (step S104). Next, the server 2 acquires the environmental information from the environment DB 32 based on the movement history information.

If there is no environmental information corresponding to the movement history information, that is, the environmental information of each area through which the user has passed is not stored in the environment DB 32 (step S105; No), the server 2 verifies the disease of the user based on the biometric information, and calculates the possibility that the user is infected with the disease (step 108). On the other hand, if there is the environmental information corresponding to the movement history information (step S105; Yes), the server 2 acquires the environmental information of each area through which the user has passed from the environment DB 32 (step S106).

The server 2 verifies the disease of the user based on the acquired environmental information and the biometric information, and calculates the possibility that the user is infected with the disease (step S107). If the probability of suffering from the disease is calculated, the server 2 determine whether the probability is equal to or greater than a threshold value (step S109).

If the probability of suffering from the disease is less than the threshold value (step S109; No), the server 2 diagnoses the user as healthy, and goes to a process of step S111. On the other hand, if the probability of suffering from the predetermined disease is equal to or greater than the threshold value (step S109; Yes), the server 2 diagnoses that the user is suffering from the disease, and makes a medical appointment in cooperation with the hospital system 4 (step S110). Next, the server 2 reports a diagnostic result to the user (step S111). Specifically, the server 2 reports, as a result, the user diagnosed as healthy, that the medical consultation by the doctor is unnecessary. On the other hand, the server 2 reports, as the result, the user diagnosed as suffering from the predetermined disease that the medical consultation by the doctor is necessary and the date and time of the medical appointment made to the hospital.

Moreover, if the user is diagnosed as suffering from the predetermined disease, the server 2 updates the report DB 33 by storing information in which the refugee ID of the infected user is associated with the symptom and the disease name, the movement history information, and the outbreak region, and the state of the outbreak region (step S112).

Next, the server 2 refers to the user DB 31 based on the movement history information of the infected user and the outbreak region stored in the report DB 33, specifies, as the high-risk user, the user who visited the same area at the same timing as the infected user, and alerts the user (step S113). Thus, the health management process is terminated.

Note that in the present disclosure, in a chase where the user is diagnosed as suffering from the predetermined disease, the server 2 makes the medical appointment in cooperation with the hospital system 4, but is not limited thereto. Instead of making the medical appointment, the server 2 may simply report the user of the result that the medical consultation by the doctor is necessary, thereby prompting the user to seek a medical consultation of the doctor. Moreover, the server 2 may send information concerning the symptom of the user and the estimated disease name to the hospital system 4 as a counseling report, and propose a preferential medical consultation of the infected user to the doctor, or repot a treatment proposal to the doctor.

Accordingly, the server 2 assists the infected user to receive the medical consultation preferentially based on the state of each of areas and the symptoms of users who visited the areas. By this assistant, it is possible to improve the efficiency of medical consultations by doctors. Moreover, based on the state of each area and an actual condition of the disease by which each user is infected in that state, it is possible to alert the user with a history of visiting that area and prompt the user to seek a medical consultation from the doctor at an appropriate timing. Therefore, it is possible for the server 2 to improve efficiency of each medical service and provide treatment tailored to the needs of each individual.

Environmental Information Collection Process

Figure 6:
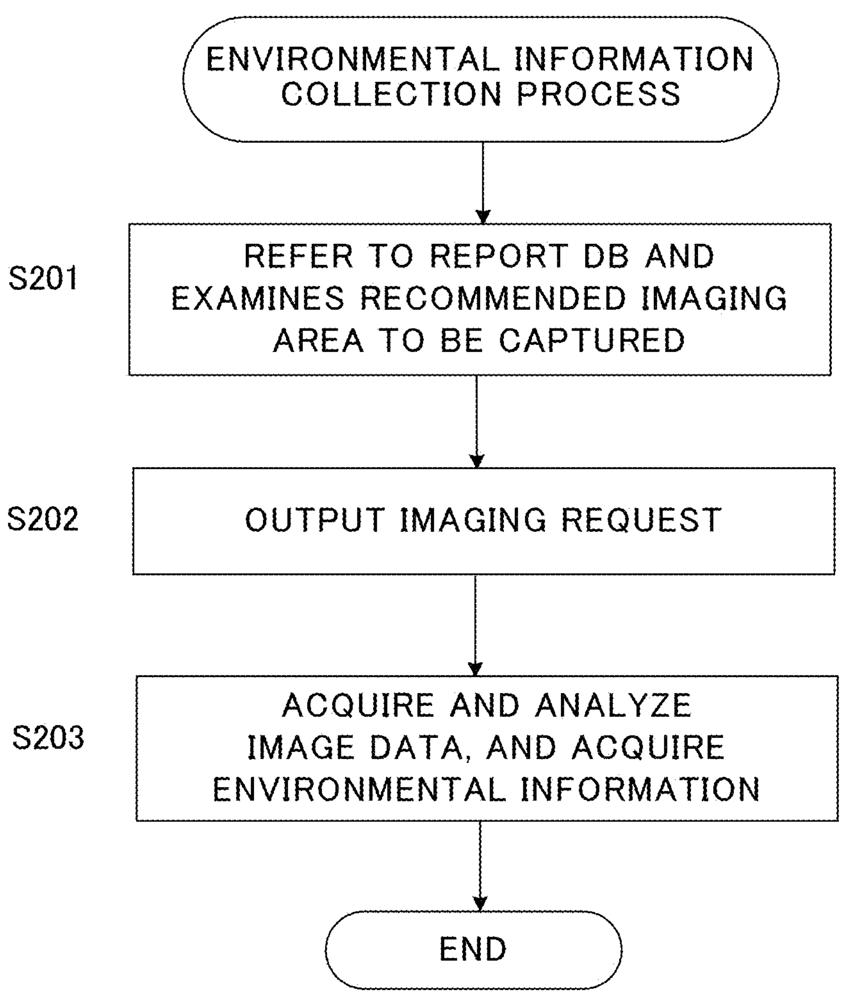
FIG. 6 illustrates a flowchart of an environmental information collection process.

Next, the environmental information collection process by the server 2 will be described. FIG. 6 is a flowchart of the environmental information collection process performed by the server 2. This environmental information collection process is realized by executing a corresponding program prepared in advance by the processor 12 illustrated in FIG. 2.

If the infected user passes the area be surveyed by the artificial satellite, the server 2 refers to the report DB 33 and examines the recommended imaging area based on the movement history information of the infected user and the outbreak region (S201). Next, the server 2 creates an imaging request which specifies the area to be captured for checking the state, and transmits the request to the satellite system 3 (step S202). The satellite system 3 captures images of the area designated by the artificial satellite and transmits satellite images to the server 2. The server 2 acquires the environmental information by analyzing the satellite images acquired from the satellite system 3, and updates the environment DB 32 (step S203). After that, the environmental information collection process is terminated.

In the manner described above, it is possible for the server 2 to accurately understand what information is desired to be acquired next based on previous satellite images and information concerning the health care of the user, and to make an appropriate imaging request which specifies a next imaging location by the artificial satellite. In other words, it is possible to predict a damage situation from the state of each area and the symptom of the user who visited that area, and it is possible to send the appropriate imaging request to the satellite system 3.

Moreover, it is possible for the server 2 to make the imaging request in consideration of quantitative information concerning the user who have actually visited the area acquired by the health management system 100, while utilizing information from open sources such as a television, a magazine, the Internet, and the like. Therefore, it is possible to realize the imaging request with higher accuracy.

First Modification

The state of the region area not limited to the disaster, but may be a state of crime. For instance, it is assumed that a region E has a high crime rate, and that a power line is artificially disconnected due to a robbery and the like, resulting in a power outage. In this case, the environmental information is, for instance, information which associates the state in area E such as a man-made power outage, with the fact that there are a large number of injuries due caused by assault and injury in the region E as a result of the power outage.

Second Modification

In the example embodiment described above, the server 2 authenticates each user using the face image acquired from the input terminal 1, but the present disclosure is not limited thereto. Any method such as a fingerprint authentication, a vein authentication, a voice authentication, and an iris authentication can be applied if an authentication method is performed based on the biometric information which the server 2 acquires from the input terminal 1.

Third Modification

The result of the initial counseling diagnosis and alert information are sent to the user in accordance with the contact details; however, in a case where the user does not have a smartphone or the like and there is no contact details, the result and the alert information may be sent to the input terminal 1, or be presented to the user by a staff or the like at the refugee camp receiving by a predetermined terminal and posting the result and the alert information.

Fourth Modification

In the example embodiments described above, the server 2 specifies the outbreak region or recognizes the conditions of the outbreak region, by referring to each DB, and creates the imaging request, but the processes of the server 2 are not limited thereto, and the server 2 may create the imaging request using the machine learning model. In this case, the server 2 creates the imaging request according to the symptom and the movement history information of the infected user by using the machine learning model which is trained to output an optimized imaging request in accordance with the symptom and the movement history information of each user. After that, the server 2 transmits the imaging request output from the machine learning model to the satellite system 3.

A part or all of the example embodiments (including the modifications, the same hereinafter) described above may also be described as the following supplementary notes, but not limited thereto.

Supplementary note 1

A health management device comprising:

an environment storage unit configured to store environmental information in which a state of a region is associated with a disease in the state;

a user identification information acquisition means configured to acquire user identification information for identifying a user;

a biometric information acquisition means configured to acquire biometric information of the user;

an authentication means configured to authenticate the user by comparing biometric information associated with the user identification information in advance with the biometric information acquired by the biometric information acquisition means;

a movement history acquisition means configured to acquire movement history information concerning each area through which the user passed, based on the user identification information;

an environmental information acquisition means configured to acquire the environmental information of each area through which the user passed from the environment storage unit, based on the movement history information;

a disease verification means configured to calculate a probability that the user is infected with the disease based on the biometric information and the environmental information; and a persuasion information output means configured to output persuasion information for persuading the user to seek a medical consultation of a doctor in a response to the probability that is equal to or greater than a threshold value.

Supplementary note 2

The health management device according to supplementary note 1, wherein the health management device is connected to a system of a satellite, and the environmental information stored in the environment storage unit is acquired from the satellite.

Supplementary note 3

The health management device according to supplementary note 2, wherein the biometric information includes a face image and a body temperature of the user, and the disease verification means specifies the disease of the user based on the face image and the body temperature, calculates the probability that the user is infected with the disease based on the disease which is specified, and information of the disease in the state of each area through which the user passed, and estimates a disease name of the disease.

Supplementary note 4

The health management device according to supplementary note 3, wherein the health management device is connected to a system of a hospital, and the health management device further includes an appointment means configured to transmit information including the user identification information and one of or both a symptom of the user and the disease name, and to make a medical appointment of the user to the system of the hospital.

Supplementary note 5

The health management device according to supplementary note 3, further including a report storage unit configured to store report information in which the user identification information is associated with one of or both a symptom of the user and the disease name, the movement history information, and the state of each area through which the user passed;

a high-risk user specifying means configured to specify each user who may be infected with a same disease as the user infected with the disease to be a high-risk user based on the report information and the movement history information of a plurality of users; and an alert information output means configured to output alert information for alerting the high-risk user.

Supplementary note 6

The health management device according to supplementary note 5, wherein the movement history information includes information of a date and time if the user visited each area, the heals management device further includes an outbreak region specifying unit configured to specify an area where the infected user encountered a state leading to the disease the disease, as an outbreak region based on the report information, the report storage unit stores the report information in which the user identification information of the infected user is associated with one of or both the symptom and the disease name, the outbreak region, a date and time if the infected user visited the outbreak region, and the high-risk user specifying means specifies, as the high-risk user, each user who visited the outbreak region during a predetermined period as the date and time if the infected user visited is to be a reference date and time.

Supplementary note 7

The health management device according to supplementary note 3, wherein the disease verification means includes a face determination means configured to determine whether or not one or more of a shape and color of a facial area is abnormal, based on a face image of the user;

a body temperature determination means configured to determine whether or not a body temperature of the user is equal to or greater than a threshold value; and an initial symptom determination means configured to determine, by using a machine learning model trained to output whether or not an initial symptom of the disease appearing on a face in response to an input of the face image, whether or not the initial symptom is appeared based on the face image of the user, wherein based on respective results of the face determination means, the body temperature determination means, and the initial symptom determination means, the symptom of the user is specified, a probability that the user is infected with the disease is calculated, and the disease name is estimated.

Supplementary note 8

The health management device according to supplementary note 1, wherein the environmental information includes one or more of information in which a flood as the state of the region is associated with a pathogen which is increasing in the region due to the flood, information in which a fire as the state of the region is associated with a large number of injuries in the region due to the fire, and information in which a landmine as the state of the region is associated with a large number of leg injuries by metal fragments in the region due to the landmine.

Supplementary note 9

A health management method to be executed by a health management device including an environment storage unit configured to store environmental information in which a state of a region is associated with a disease in the state, the health management method comprising:

acquiring user identification information for identifying a user;

performing a biometric information acquisition process for acquiring biometric information of the user;

authenticating the user by comparing biometric information associated with the user identification information in advance with the biometric information acquired by the biometric information acquisition process;

acquiring movement history information concerning each area through which the user passed, based on the user identification information;

acquiring the environmental information of each area through which the user passed from the environment storage unit, based on the movement history information;

calculating a probability that the user is infected with the disease based on the biometric information and the environmental information; and outputting persuasion information for persuading the user to seek a medical consultation of a doctor in a response to the probability that is equal to or greater than a threshold value.

Supplementary note 10

A program causing a computer to perform a process, wherein a health management device includes an environment storage unit configured to store environmental information in which a state of a region is associated with a disease in the state, and the computer, the process comprising:

acquiring user identification information for identifying a user;

performing a biometric information acquisition process for acquiring biometric information of the user;

authenticating the user by comparing biometric information associated with the user identification information in advance with the biometric information acquired by the biometric information acquisition process;

acquiring movement history information concerning each area through which the user passed, based on the user identification information;

acquiring the environmental information of each area through which the user passed from the environment storage unit, based on the movement history information;

calculating a probability that the user is infected with the disease based on the biometric information and the environmental information; and outputting persuasion information for persuading the user to seek a medical consultation of a doctor in a response to the probability that is equal to or greater than a threshold value.

While the present disclosure has been described with reference to the example embodiments and examples, the present disclosure is not limited to the above example embodiments and examples. Various changes which can be understood by those skilled in the art within the scope of the present disclosure can be made in the configuration and details of the present disclosure.

This application is based upon and claims the benefit of priority from Japanese Patent Application 2024-035053, filed on Mar. 7, 2024, the disclosure of which is incorporated herein in its entirety by reference.

DESCRIPTION OF SYMBOLS

- 1 Input terminal
- 2 Server
- 3 Satellite system
- 4 Hospital system
- 5 Network
- 11 Interface
- 12 Processor
- 13 Memory
- 14 Recording medium
- 15 Display unit
- 16 Input unit
- 31 User DB
- 32 Environment DB
- 33 Report DB
- 100 Health management system

The invention claimed is:

1. A health management device comprising:

at least one memory configured to store instructions;

an environment storage unit configured to store environmental information in which a state of a region is associated with a disease in the state; and at least one processor configured to execute the instructions to:

acquire user identification information for identifying a user;

acquire biometric information of the user;

authenticate the user by comparing biometric information associated with the user identification information in advance with the biometric information which is acquired;

acquire movement history information concerning each area through which the user passed, using the user identification information;

acquire the environmental information of each area through which the user passed from the environment storage unit, using the movement history information;

determine, by using a machine learning model trained to determine whether or not an initial symptom of the disease appears on a face, whether or not the initial symptom has appeared using a face image included in the biometric information;

calculate a probability that the user is infected with the disease using the biometric information and the environmental information and a result of determining whether or not the initial symptom has appeared;

in a response to the probability being less than a threshold value, output a notification to a contact address of the user that a medical consultation by a doctor is unnecessary; and in response to the probability being equal to or greater than the threshold value:

create an imaging request specifying an outbreak region where the user encountered a state leading to the disease;

transmit the created imaging request to a satellite system to cause the satellite system to capture a new satellite image for updating the environmental information; and make a medical appointment for the user by transmitting information including the user identification information to a hospital system.

2. The health management device according to claim 1, wherein:

the health management device is connected to a system of a satellite, and the environmental information stored in the environment storage unit is acquired from the satellite.

3. The health management device according to claim 2, wherein:

the biometric information includes a face image and a body temperature of the user, and the at least one processor is configured to execute the instructions to specify the disease of the user using the face image and the body temperature, calculate the probability that the user is infected with the disease using the disease which is specified, and information of the disease in the state of each area through which the user passed, and esestimate a disease name of the disease.

4. The health management device according to claim 3, wherein:

the health management device is connected to a system of a hospital, and the at least one processor is configured to execute the instructions to transmit information including the user identification information and at least one of a symptom of the user and the disease name, and to make a medical appointment of the user to the system of the hospital.

5. The health management device according to claim 3, further comprising:

a report storage unit configured to store report information in which the user identification information is associated with one of or both a symptom of the user and the disease name, the movement history information, and the state of each area through which the user passed, wherein the at least one processor is configured to execute the instructions to:

specify each user who may be infected with a same disease as the user infected with the disease to be a high-risk user using the report information and the movement history information of a plurality of users; and output alert information for alerting the high-risk user.

6. The health management device according to claim 5, wherein:

the movement history information includes information of a date and time if the user visited each area, the heals management device further includes an outbreak region specifying unit configured to specify an area where the infected user encountered a state leading to the disease the disease, as an outbreak region using the report information, the report storage unit stores the report information in which the user identification information of the infected user is associated with one of or both the symptom and the disease name, the outbreak region, a date and time if the infected user visited the outbreak region, and the at least one processor is configured to execute the instructions to specify, as the high-risk user, each user who visited the outbreak region during a predetermined period as the date and time if the infected user visited is to be a reference date and time.

7. The health management device according to claim 5, wherein the at least one processor is configured to execute the instructions to:

determine whether or not one or more of a shape and color of a facial area is abnormal, using a face image of the user;

determine whether or not a body temperature of the user is equal to or greater than a threshold value; and determine, by using a machine learning model trained to output whether or not an initial symptom of the disease appearing on a face in response to an input of the face image, whether or not the initial symptom is appeared using the face image of the user, wherein using respective results of determining whether or not whether or not one or more of a shape and color of a facial area is abnormal, determining whether or not a body temperature of the user is equal to or greater than a threshold value, determining whether or not the initial symptom is appeared, the symptom of the user is specified, a probability that the user is infected with the disease is calculated, and the disease name is estimated.

8. The health management device according to claim 1, wherein the environmental information includes one or more of:

information in which a flood as the state of the region is associated with a pathogen which is increasing in the region due to the flood, information in which a fire as the state of the region is associated with a large number of injuries in the region due to the fire, and information in which a landmine as the state of the region is associated with a large number of leg injuries by metal fragments in the region due to the landmine.

9. A health management method to be executed by a health management device including an environment storage unit configured to store environmental information in which a state of a region is associated with a disease in the state, the health management method comprising:

acquiring user identification information for identifying a user;

performing a biometric information acquisition process comprising acquiring biometric information of the user;

authenticating the user by comparing biometric information associated with the user identification information in advance with the biometric information acquired by the biometric information acquisition process;

acquiring movement history information concerning each area through which the user passed, using the user identification information;

acquiring the environmental information of each area through which the user passed from the environment storage unit, using the movement history information;

determining, by using a machine learning model trained to determine whether or not an initial symptom of the disease appears on a face image, whether or not the initial symptom has appeared using face image included in the biometric information;

calculating a probability that the user is infected with the disease using the biometric information and the environmental information and a result of determining whether or not the initial symptom has appeared;

in a response to the probability being less than a threshold value, outputting a notification to a contact address of the user that a medical consultation by a doctor is unnecessary; and in response to the probability being equal to or greater than the threshold value:

creating an imagining request specifying an outbreak region where the user encountered a state leading to the disease;

transmitting the created imaging request to a satellite system to cause the satellite system to capture a new satellite image for updating the environmental information; and making a medical appointment for the user by transmitting information including the user identification information to a hospital system.

10. A non-transitory computer-readable program causing a computer to perform a process, wherein a health management device includes an environment storage unit configured to store environmental information in which a state of a region is associated with a disease in the state, and the computer, the process comprising:

acquiring user identification information for identifying a user;

performing a biometric information acquisition process comprising acquiring biometric information of the user;

authenticating the user by comparing biometric information associated with the user identification information in advance with the biometric information acquired by the biometric information acquisition process;

acquiring movement history information concerning each area through which the user passed, using the user identification information;

acquiring the environmental information of each area through which the user passed from the environment storage unit, using the movement history information;

determining, by using a machine learning model trained to determine whether or not an initial symptom of the disease appears on a face image, whether or not the initial symptom has appeared using face image included in the biometric information;

calculating a probability that the user is infected with the disease using the biometric information and the environmental information and a result of determining whether or not the initial symptom has appeared;

in a response to the probability being less than a threshold value, outputting a notification to a contact address of the user that a medical consultation by a doctor is unnecessary; and in response to the probability being equal to or greater than the threshold value:

creating an imagining request specifying an outbreak region where the user encountered a state leading to the disease;

transmitting the created imaging request to a satellite system to cause the satellite system to capture a new satellite image for updating the environmental information; and making a medical appointment for the user by transmitting information including the user identification information to a hospital system.

11. The health management device according to claim 1, wherein the at least one processor is configured to execute the instructions to output, in response to the probability being equal to or greater than the threshold value, persuasion information for persuading the user to seek a medical consultation of a doctor.

12. The health management device according to claim 3, wherein the at least one processor is configured to execute the instructions to:

create an imaging request corresponding to a symptom of the user and the movement history using a machine learning model trained to output an optimized imaging request using the symptoms and the movement history; and acquire environmental information by analyzing satellite images acquired from the satellite by transmitting the optimized imaging request output from the machine learning model to the satellite.

13. The health management device according to claim 9, wherein the health management method further comprises outputting, in response to the probability being equal to or greater than the threshold value, persuasion information for persuading the user to seek a medical consultation of a doctor.

14. The non-transitory computer-readable program according to claim 10, wherein the process further comprises outputting, in response to the probability being equal to or greater than the threshold value, persuasion information for persuading the user to seek a medical consultation of a doctor.

* * * * *